(12) United States Patent
König

(10) Patent No.: US 12,420,004 B2
(45) Date of Patent: Sep. 23, 2025

(54) SYSTEM FOR VACUUM-ASSISTED VENOUS DRAINAGE (VAVD)

(71) Applicant: Irasun GmbH, Munich (DE)

(72) Inventor: Fabian König, Unterföhring (DE)

(73) Assignee: IRASUN GMBH, Munich (DE)

( * ) Notice: Subject to any disclaimer, the term of this patent is extended or adjusted under 35 U.S.C. 154(b) by 748 days.

(21) Appl. No.: 16/169,956

(22) Filed: Oct. 24, 2018

(65) Prior Publication Data

US 2019/0160277 A1 May 30, 2019

(30) Foreign Application Priority Data

Oct. 25, 2017 (DE) ..................... 10 2017 124 927.3

(51) Int. Cl.
*A61M 1/36* (2006.01)
*A61M 39/22* (2006.01)
(Continued)

(52) U.S. Cl.
CPC ........ *A61M 1/3667* (2014.02); *A61M 1/3627* (2013.01); *A61M 39/22* (2013.01); *A61B 2017/306* (2013.01); *A61M 2039/226* (2013.01); *A61M 2039/242* (2013.01); *A61M 2205/14* (2013.01); *A61M 2205/3341* (2013.01); *A61M 2205/36* (2013.01); *A61M 2205/502* (2013.01); *A61M 2205/52* (2013.01); *A61M 2205/75* (2013.01)

(58) Field of Classification Search
CPC .......... A61B 2017/306; A61M 1/3627; A61M 1/3667; A61M 2039/226; A61M 2039/242; A61M 2205/14; A61M 2205/3341; A61M 2205/36; A61M 2205/502; A61M 2205/52; A61M 2205/75; A61M 39/22
See application file for complete search history.

(56) References Cited

U.S. PATENT DOCUMENTS

| | | |
|---|---|---|
| 5,531,712 A | 7/1996 | Malcolm et al. |
| 6,017,493 A | 1/2000 | Cambron et al. |
| (Continued) | | |

FOREIGN PATENT DOCUMENTS

| | | |
|---|---|---|
| EP | 2358413 B1 | 8/2011 |
| WO | 2017046567 A2 | 3/2017 |
| (Continued) | | |

*Primary Examiner* — Kai H Weng
(74) *Attorney, Agent, or Firm* — McCoy Russell LLP

(57) ABSTRACT

The present disclosure relates to a system for vacuum-assisted venous drainage (VAVD), comprising at least one pressure regulation module, at least one active pressure regulating valve having at least one supply line and at least one discharge line, wherein further at least one pressure sensor is provided such that the pressure in the region of the pressure regulating valve can be monitored and an actual pressure value can be detected, and wherein the pressure regulating valve is designed and set up such that the negative pressure generated by the pressure regulating module can be actively regulated by the pressure regulating valve on the basis of the actual pressure value. The present disclosure further relates to an assembly comprising a system for vacuum-assisted venous drainage and a medical device as well as to a method for operating the system for vacuum-assisted venous drainage.

15 Claims, 11 Drawing Sheets

(51) Int. Cl.
*A61B 17/30* (2006.01)
*A61M 39/24* (2006.01)

(56) References Cited

U.S. PATENT DOCUMENTS

| | | | |
|---|---|---|---|
| 6,623,463 | B2 | 9/2003 | Jones et al. |
| 7,814,932 | B2 | 10/2010 | Stinson |
| 7,998,114 | B2 | 8/2011 | Lombardi |
| 8,881,763 | B2 | 11/2014 | Stinson |
| 10,099,000 | B2 | 10/2018 | Strohhoefer et al. |
| 10,124,106 | B2 | 11/2018 | Nimura et al. |
| 10,413,642 | B2 | 9/2019 | Berry et al. |
| 10,806,846 | B2 | 10/2020 | Turner |
| 2002/0085952 | A1* | 7/2002 | Ellingboe ............ A61M 1/3632 422/45 |
| 2003/0216690 | A1 | 11/2003 | Foley |
| 2009/0099498 | A1* | 4/2009 | Demers ................ A61M 60/40 604/6.09 |
| 2011/0166515 | A1 | 7/2011 | Nour |
| 2011/0282126 | A1 | 11/2011 | Nour |
| 2012/0130299 | A1 | 5/2012 | Knott et al. |
| 2012/0253257 | A1* | 10/2012 | Tamari ................ A61M 1/3667 604/6.09 |
| 2013/0020237 | A1* | 1/2013 | Wilt ....................... A61K 33/00 210/85 |
| 2014/0150789 | A1* | 6/2014 | Flanagan ............ A61M 16/122 128/203.22 |
| 2015/0246173 | A1* | 9/2015 | Steger ................ A61M 1/3656 604/6.01 |
| 2017/0189588 | A1* | 7/2017 | Croizat .................. A61M 1/96 |
| 2017/0296727 | A1* | 10/2017 | Burbank ................ A61M 1/165 |
| 2018/0104390 | A1 | 4/2018 | Kilcran |
| 2019/0022299 | A1 | 1/2019 | Schrörs et al. |
| 2019/0070353 | A1 | 3/2019 | Knott et al. |
| 2020/0054816 | A1 | 2/2020 | Frugier |
| 2020/0164124 | A1 | 5/2020 | Zuo et al. |
| 2021/0196871 | A1 | 7/2021 | Locke et al. |

FOREIGN PATENT DOCUMENTS

| | | |
|---|---|---|
| WO | 2017148984 A1 | 9/2017 |
| WO | 2018099593 A1 | 6/2018 |
| WO | 2018140414 A1 | 8/2018 |
| WO | 2018202661 A1 | 11/2018 |
| WO | 2020074357 A1 | 4/2020 |
| WO | 2020081991 A2 | 4/2020 |
| WO | 2020081995 A2 | 4/2020 |
| WO | 2020112902 A1 | 6/2020 |
| WO | 2021137116 A1 | 7/2021 |

\* cited by examiner

SYSTEM FOR VACUUM-ASSISTED VENOUS DRAINAGE (VAVD)

CROSS REFERENCE TO RELATED APPLICATION

The present application claims priority to German Patent Application No. 10 2017 124 927.3 entitled "SYSTEM FOR VACUUM-ASSISTED VENOUS DRAINAGE (VAVD)," filed on Oct. 25, 2017. The entire contents of the above-listed application are hereby incorporated by reference in their entirety for all purposes.

TECHNICAL FIELD

The present disclosure relates to a system for vacuum-assisted venous drainage (VAVD), an assembly comprising a system and a medical device, and to a method for operating a system for vacuum-assisted venous drainage (VAVD).

BACKGROUND AND SUMMARY

In a variety of cardiac surgery procedures, temporary cardiac immobilization is necessary. However, the cardiovascular circulation must be maintained almost continuously in order to ensure sufficient oxygenation of the patient. For this purpose, an extracorporeal circulation is connected to a heart-lung machine (HLM), which maintains oxygenation and blood flow. The venous patient blood is collected in the cardiotomy reservoir and then pumped through an oxygenator. The oxygenated blood is then returned to the patient via the arterial line. While the arterial recirculation is actively driven by roller or centrifugal pumps, the drainage of the patient, i.e. the blood withdrawal from the patient's body before oxygenation, is carried out passively by the Bernoulli principle. The patient and the cardiotomy reservoir are placed at different heights, resulting in a pressure difference when the tube system is prefilled, leading to a blood flow from the patient into the reservoir. This often requires long tube connections to achieve the required difference in height.

The tubing system must be filled with fluids prior to use to allow drainage and to prevent the introduction of air into the cardiovascular system. This "priming volume" should be kept as low as possible in order to avoid negative effects for the patient, hemodilution, hemolysis and inflammatory reactions. This is particularly important in pediatric patients, as the autologous blood volume is comparatively low here. The aim is therefore to keep the tubing lengths as short as possible and to minimize the diameters of the tubes and cannulas. In this way, the priming volume can be significantly reduced.

However, this strategy is limited for purely passive drainage. The pressure gradient—and consequently also the flow rate—can only be regulated by adjusting the height difference and are therefore limited. For this reason, drainage is often supported by active mechanisms. In recent years, vacuum assisted venous drainage (VAVD) has established itself. Here, a negative pressure is applied to the cardiotomy reservoir, which leads to a higher pressure gradient and thus to higher flows. In this way, the flow rate can be flexibly adjusted and there is no need for a difference in height between patient and reservoir.

By using VAVD, the priming volume can be drastically reduced and the drainage flow better controlled. The improved drainage also causes the surgical site to contain a noticeably smaller amount of blood and makes work easier.

For the safe and efficient functioning of VAVD, it is crucial that the negative pressure in the cardiotomy reservoir is precisely controlled. This requires the use of VAVD controllers to control the high negative pressure of the vacuum lines to the desired negative pressure. There are only a few dedicated VAVD controllers, all of which are based on mechanical proportional pressure regulators. However, this poses a number of disadvantages and risks and is therefore not optimal.

In all currently available VAVD controllers, the vacuum in the cardiotomy reservoir is adjusted using a mechanical proportional pressure valve. Therefore, no target value is set, but the opening angle of the valve is adjusted and the actual minus value is read off an integrated manometer. As long as the pressure and flow conditions remain constant, this is not yet a disadvantage. However, aspirators are often used during the operation to draw blood from the surgical site and to transfer it to the cardiotomy reservoir for recovery. However, this generates a volume flow into the reservoir and thus counteracts the set negative pressure. The cardio technician must therefore correct the opening angle of the valve several times during the operation, as dynamic regulation is not possible here. However, this poses a high risk, especially at the end of the operation: Since all aspirators are switched off simultaneously, the positive volume flow into the reservoir is eliminated and the set opening angle on the VAVD controller leads to huge negative pressures in the reservoir. This leads to excessive drainage of the patient, causing the cardiotomy reservoir to fill rapidly and, in the worst case, patient blood to penetrate the VAVD tubing set and VAVD controller. In addition, the enormous negative pressures can also have negative effects on the patient's blood.

A further disadvantage of the previous VAVD controllers is the lack of control of the actual state in the reservoir. Disturbances such as too low pressures or pressure peaks can only be checked by human control. An excessively low pressure in the reservoir may induce the formation of microbubbles, which can lead to air embolisms and thus also pose a considerable risk.

There is therefore an acute clinical need for a system that eliminates these disadvantages and enables safe VAVD.

VAVD systems are known, for example, from U.S. Pat. No. 6,017,493.

A control valve for a medical suction device is known from U.S. Pat. No. 5,531,712.

Document U.S. Pat. No. 6,623,463 B2 relates to a medical vacuum system, as does U.S. Pat. No. 7,814,932 B2 or U.S. Pat. No. 8,881,763 B2.

US 2003/0216690 A1 and U.S. Pat. No. 7,998,114 B2 provide solutions for pressure regulation in medical operations.

US 2012/0130299 A1 relates to a device for taking blood samples from a patient into a blood reservoir of an extracorporeal blood circulation.

This object is achieved according to the disclosure by a system for vacuum-assisted venous drainage (VAVD). According to this, provision is made that a system for vacuum-assisted venous drainage (VAVD) is provided with at least one pressure regulating module (which may be a negative pressure regulating module), with at least one active pressure regulating valve having at least one supply line and at least one discharge line, wherein further at least one pressure sensor is provided, by means of which the pressure in the region of the pressure regulating valve can be monitored and an actual pressure value can be detected, and the pressure regulating valve being designed and set up in such a way that, by means of the pressure regulating valve and on the basis of the actual pressure value, the negative pressure generated by the pressure regulating module can be actively regulated.

The disclosure is based on the basic idea that the actual pressure in the system or reservoir is measured and the pressure valve can be automatically readjusted to achieve the desired target value. This also allows a safe pressure range to be defined and maintained. In the event of a limit being exceeded, an appropriate monitoring and alerting can also be achieved in this context. By adjusting to an actual pressure value, the negative pressure generated can be actively regulated by the negative pressure generation module. Abrupt pressure changes, such as at the end of an operation, can be quickly and safely regulated accordingly by such a control, whereby, for example, a massive pressure drop or rapid pressure changes can be prevented. This allows a quick reaction to changing environmental influences and an even pressure control and even pressure conditions in the system can be guaranteed. The vacuum is therefore no longer regulated manually, but via an electric or automatic pressure and vacuum regulator. This can be integrated into the active pressure regulating valve. The pressure control is configured in such a way that the pressure control is given a ramp when the pressure rises, so that the resulting suction is increased only slowly and the patient's blood can therefore be protected even better. On the other hand, the pressure control can react even faster when the desired pressure drop occurs, so that this results in relaxation and a mitigation of a risk situation for the patient. In particular, it is conceivable that the pressure sensor integrated in the electrical control valve continuously checks the actual pressure value and automatically readjusts the mixing ratio accordingly. This guarantees that the pressure value specified by the user is reached and maintained even under changing ambient conditions or pressure changes. In this context, it may also be provided that the pressure sensor can be installed within the structural limits defined by the system. As an alternative or additional solution, it is also conceivable that the reservoir may have a (further) sensor, in particular a pressure sensor. This further pressure sensor may be arranged particularly advantageously within the reservoir. Due to this assembly of the pressure sensor, the accuracy of the measurement on the one hand and of the pressure control on the other hand is further optimized. The transfer of the reservoir pressure recorded by the pressure sensor to the system may be wireless and/or wired.

In addition, it may be provided that the system further comprises a hose set for fluid guidance within the system as well as a presence detection unit (PDU), the correct placement and connection of the hose set being able to be monitored and/or verifiable by means of the presence detection unit (PDU). By integrating the presence detection unit (PDU) in combination with a hose set accessory, the presence of fluids in the hose set can be made possible. The presence detection unit (PDU) may be designed such that safe placement of the fluid reservoir can be checked and guaranteed. A presence sensor of the presence detection unit (PDU) may continuously monitor and detect the correct placement of the liquid reservoir. For example, another presence sensor may monitor the inside of the fluid reservoir and monitor any type of incoming fluids.

The hose set may further have at least one fluid reservoir and the presence detection unit (PDU) can monitor and verify the correct placement and connection of the fluid reservoir. By integrating the fluid reservoir into a hose set, it is also possible to detect fluid aspiration in good time so that the system automatically returns to a safe state and liquid penetration into the system is prevented. The sensors of the presence detection unit (PDU) can be calibrated to this. The reservoir may be mechanically fixed in the vacuum regulator, whereby a correct alignment and a defined distance to the sensors can be guaranteed. The reservoir may be dimensioned such that the fluid flow is delayed long enough to guarantee a timely shutdown of the system before fluids can enter the system.

In addition, the pressure regulating valve may be provided with at least one controllable proportional pressure valve in which the pressure sensor is integrated.

The system may have at least one mechanical vacuum safety valve which is in fluid communication with the pressure regulating valve and opens at an adjustable actual pressure value. The mechanical vacuum safety valve may be an analog safety valve. A mechanical limitation can ensure that a safe vacuum range is maintained, as the maximum negative pressure can be mechanically limited. The vacuum safety valve can thus be configured in such a way that the maximum negative pressure cannot be exceeded. Mechanical vacuum safety valves can be used, for example, to ensure that they open at maximum negative pressure. In particular, it is conceivable to integrate such valves redundantly (i.e. at least two valves) or with multiple redundancy into the system in order to be able to compensate for any undetected failure of system components if possible.

Furthermore, it may be provided that the pressure regulating valve has at least one electrical and/or electronic pressure limiting element. These may be electronic safety actuators which can actuate the pressure regulating valve.

It may also be provided that the system has an inputs and outputs (such as a user interface) by means of which the user is able to input operating parameters, in particular desired values and/or target values and/or product limits and/or maximum limits, and by means of which operating parameters can be output, in particular displayed. The system may thus have a graphical user interface, via which target values, warning limits and maximum limits can be defined by the user. By a simple and intuitive input possibility a guided user input can be made possible and operating errors can be prevented. Errors may lead to acoustic warning messages as well as to visual warning messages, which can be output via the graphical user interface. It is also conceivable that the error causes can also be described on the user interface. It is also conceivable that illustrations for troubleshooting can be displayed or concrete instructions for the next steps in the treatment process can be provided.

Furthermore, the system may be provided with an operating parameter recording module by means of which operating parameters of the system can be monitored and/or recorded. Using such a system, application data such as date, runtime, target value, actual value, warning limits, maximum limits or other operating parameters can be archived in the system in an internal memory. It is also conceivable that the operating parameter recording module is connected to an external storage system in order to archive application data there. For example, in the event of a dispute, the actual pressure processes in the system can be documented and user errors can be ruled out. In addition, such a system can be used for quality assurance.

In particular, it is also conceivable that the operating parameter recording module has a patient data management interface by means of which data can be exchanged with a patient data management system. Such a facility will make it possible to simplify data recording and data management associated with the system for patient treatment.

In addition, it may be provided that the system has a synchronization interface by means of which data can be exchanged with one or more medical devices, in particular wherein at least one stop command for activating or deactivating the negative pressure generation module can be exchanged via the synchronization interface. It is conceivable, for example, that a serial interface or other interface with a data input is provided for this purpose. By means of the interface and the corresponding signals transmitted and exchanged via it, other medical devices can switch off or on the vacuum by sending a stop command. This allows the automated synchronization of processes that previously had to be performed manually. The automation of the synchronization increases in particular the user-friendliness and, if necessary, the safety of the patient.

In addition, the system may be provided with sterile filters, whereby the inlets and outlets as well as the inlet and outlet of the system are sterilely sealed by means of the sterile filters. By sealing the system at all inlets and outlets with sterile filters, it is possible to ensure contamination-proof aspiration by means of the system. This ensures that the system cannot be contaminated and that contaminated air cannot be discharged into the vacuum line or the environment. This increases the operational safety of the entire system.

In addition, provision can be made that the system has a safe mode in which the supply line is closed and the discharge to the atmosphere is activated at the same time. This allows a safe pressure-less state to be achieved where the system is configured to set a safe mode in the stop mode, in the event of a fault or loss of supply voltage. This guarantees that the supply line to the vacuum source is closed and that the secondary line to the atmosphere is activated at the same time. An undesired pressure build-up or an undesired pressure fluctuation in the secondary line can thus be avoided.

It may also be provided that the safe mode is activated or can be automatically activated in the event of a system stop and/or in the event of a fault and/or loss of supply voltage.

In addition, the present disclosure relates to an assembly comprising at least one system for vacuum-assisted venous drainage (VAVD) and to at least one medical device. The medical device may in particular be a heart-lung machine, a hypothermia device or a medical fixation device working with vacuum.

Furthermore, the present disclosure relates to a method for operating a system for vacuum-assisted venous drainage (VAVD), the method comprising at least the following steps:

the pressure in the system is monitored and measured pressure values are continuously generated, an actual pressure value is generated on the basis of these measured pressure values, and the negative pressure generated by the negative pressure generation module is actively regulated and/or controlled on the basis of the actual pressure value by means of the pressure regulating valve.

BRIEF DESCRIPTION OF THE FIGURES

Further details and advantages of the disclosure will now be explained by means of an exemplary embodiment described in more detail in the drawings in which.

DETAILED DESCRIPTION

Figure 1:
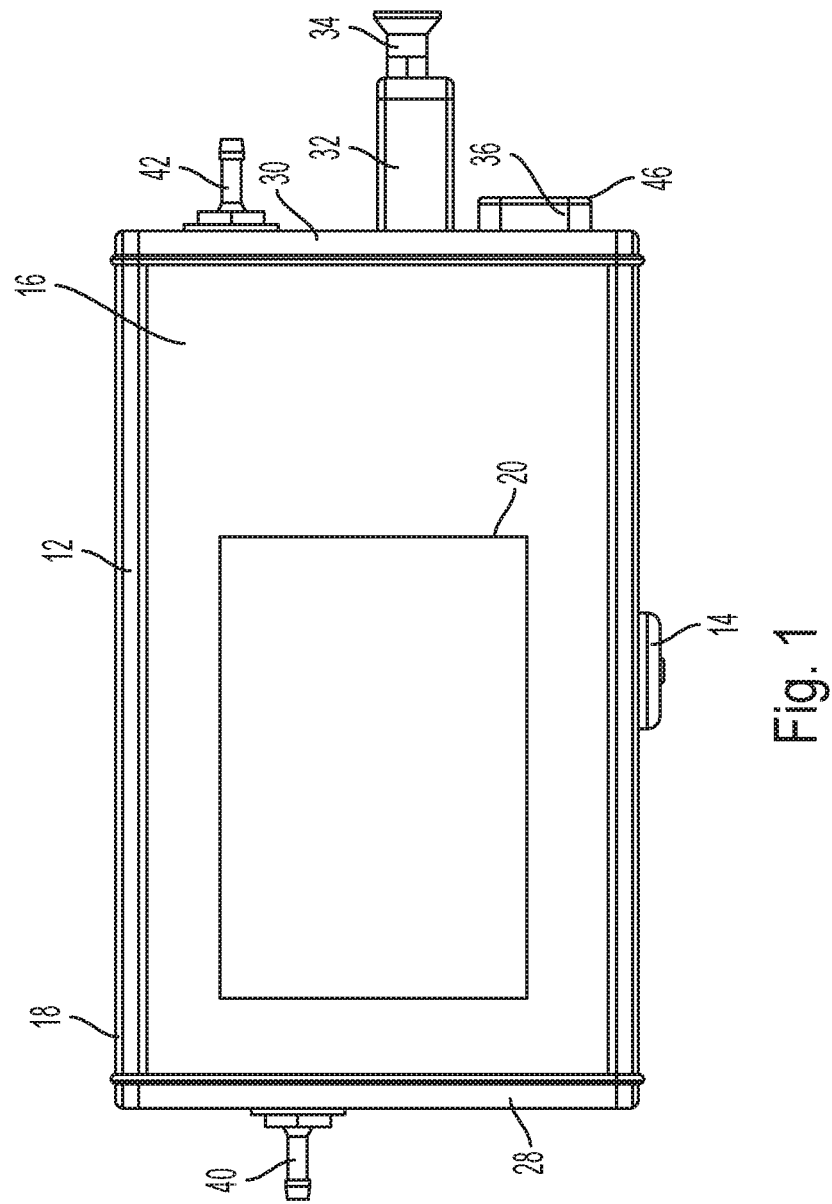
FIG. 1 is a schematic overview of an exemplary embodiment of a system according to the disclosure for vacuum-assisted venous drainage (VAVD)

FIG. 1 shows in a schematic representation of the assembled system 10 for vacuum-assisted venous drainage (VAVD) or generally for active regulation of the negative pressure.

Figure 2:
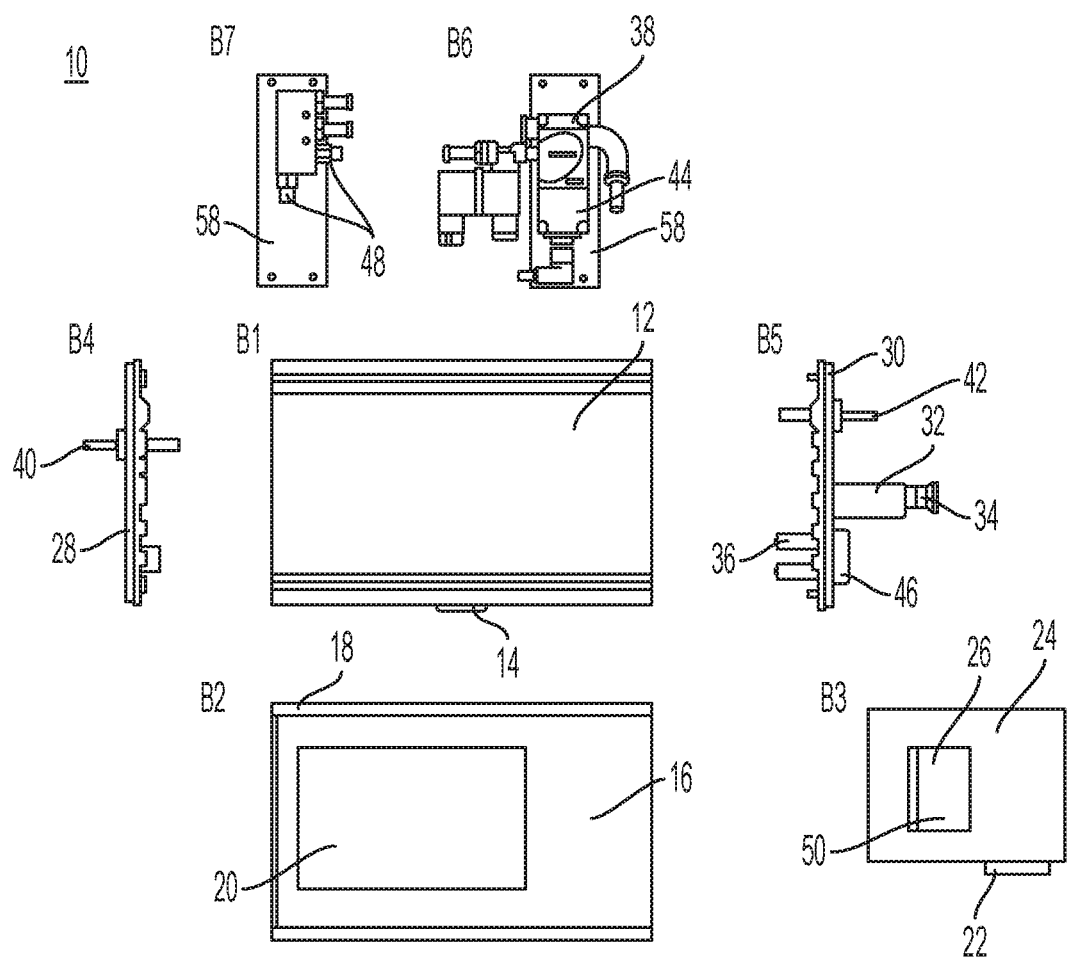
FIG. 2 shows the system from FIG. 1 disassembled into the individual assembly units B1-B7.

The system 10 consists of several assembly units B1-B7, which are individually pre-assembled and then screwed together. This allows a simplified construction and a better examination of the assembled system and the individual assembly units. FIG. 2 is a schematic illustration of the assembly units of the system 10 in an exploded view.

The system 10 has a housing 12 as assembly unit B1, which is e.g. provided as a U-profile with a mounted multi-function holder or else several multi-function holders.

Figure 9:
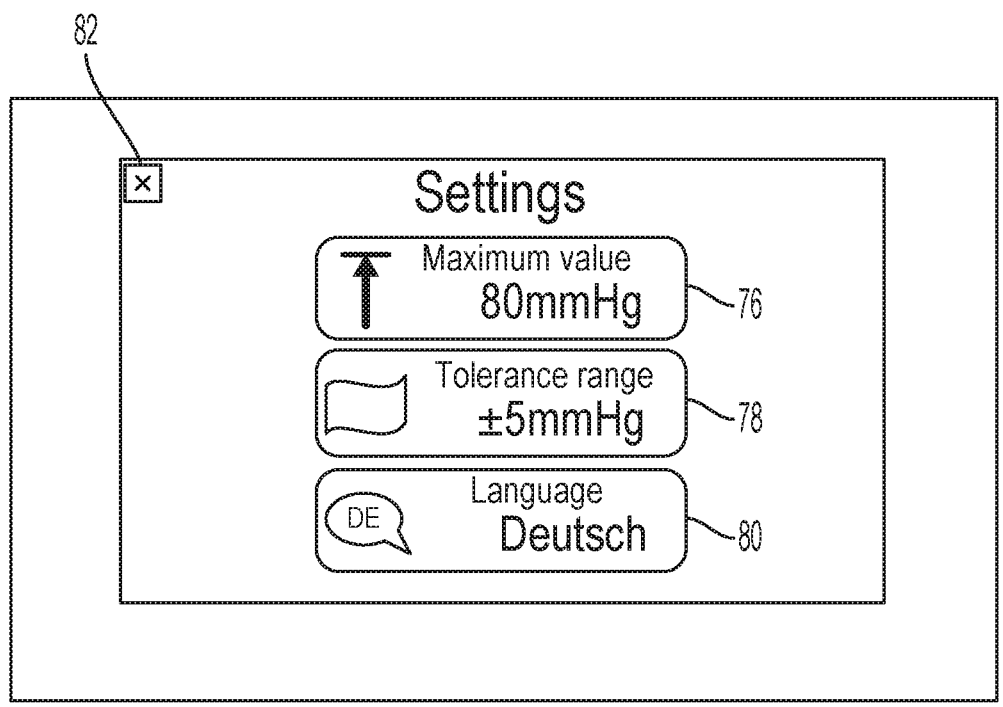
FIG. 9 shows a graphical representation of the settings that can be made via a setup menu of the graphical user interface indicated by the display.
Figure 10:
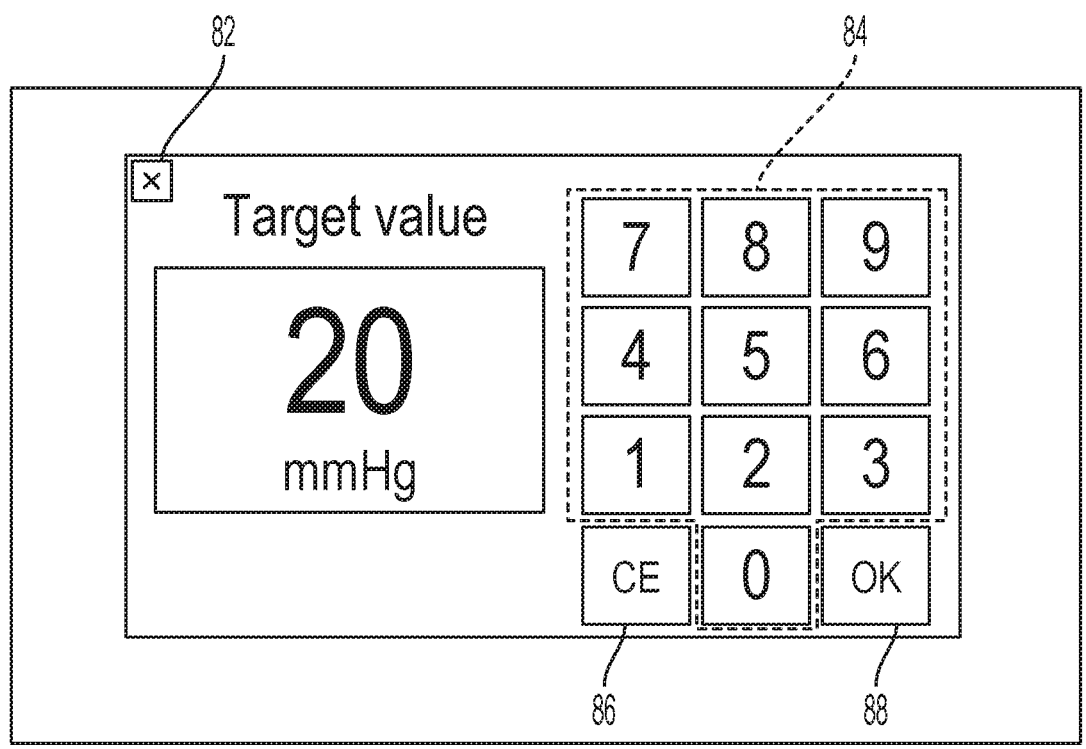
FIG. 10 shows a graphical representation of a data input menu of the graphical user interface indicated by the display.
Figure 11:
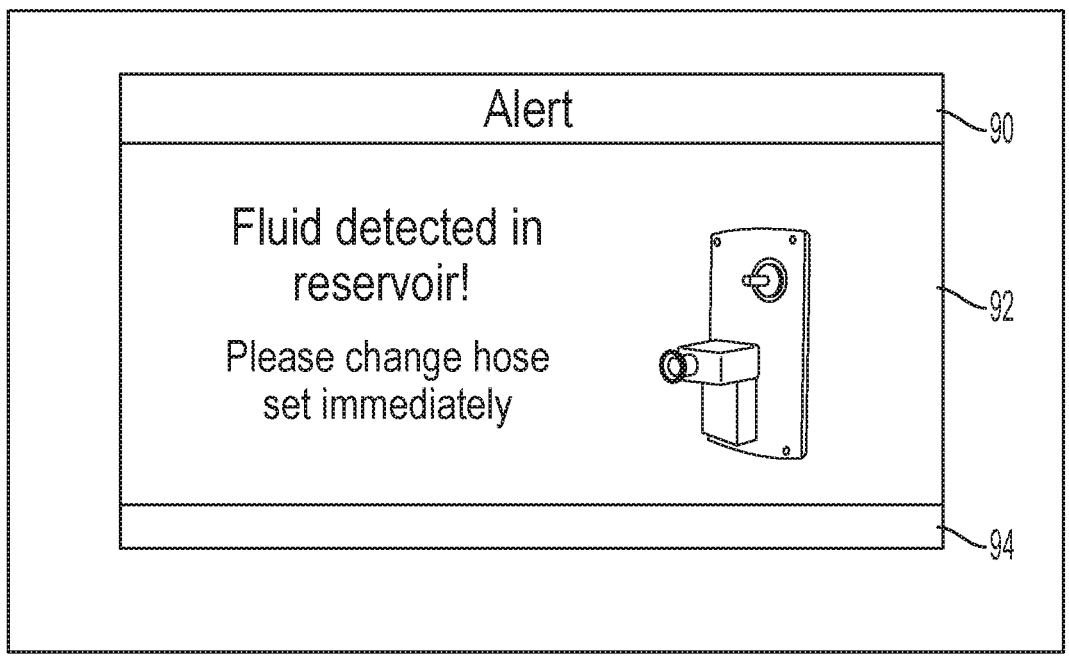
FIG. 11 shows a graphical representation of a visual error message of the graphical user interface indicated by the display.

As shown in FIG. 2, the assembly unit B2 is the front cover 16 comprising the housing cover 18 with an integrated display 20 (see also FIG. 9-11). The control unit, comprising touch controller 22 as well as the backend board 24 and control board 26 form the assembly unit B3. This is mounted on the rear side of the housing cover 18.

Accordingly, the housing cover 18 is part of the front cover 16, whereby it is also conceivable that the housing cover 18 forms the front cover. It is further conceivable that the housing cover is completely made of glass to provide a surface that is as hygienic as possible and easy to clean.

The primary interface is the B4 module and, as a cover plate left 28, provides an interface for supply lines, data exchange and power supply.

The cover plate right 30 forms a further assembly unit, namely the assembly unit B5, and serves as a secondary interface to the patient, including a reservoir holder 32 and the corresponding sensor system 36.

The reservoir holder 32 also has a quick-release mechanism 34 for fixing the reservoir.

The system 10 also has a pressure regulation module, the assembly unit B6, arranged in the housing 12. An active pressure regulating valve 38 is also provided, which has at least one supply line 40 and at least one discharge line 42. The supply line 40 and the discharge line 42 can be arranged in the cover plates 28 and 30.

The system 10 also has a pressure sensor 44.

The pressure sensor 44 can be used to monitor the pressure in the area of the pressure regulating valve 38 and to record an actual pressure value.

To this end, the pressure regulating valve 38 has a controllable proportional pressure valve in which the pressure sensor 44 is integrated.

For this purpose, the pressure regulating valve 38 can be connected to a corresponding control board 26 and/or backend board 24.

The pressure regulating valve 38 can also be designed and set up in such a way that the negative pressure generated by the pressure regulating module B6 can be actively regulated by means of the pressure regulating valve 38 on the basis of the actual pressure value.

The system 10 also has a presence detection unit 46 on the assembly unit B5 and the cover plate 30, which can be used to monitor and verify the correct placement and proper connection of a fluid reservoir of a hose set (not shown in detail). In addition, the presence detection unit 46 can detect the penetration of fluids into the liquid reservoir and report this to the control board 26 or backend board 24.

For this purpose, the presence detection unit 46 may contain the sensor system 36 or it is also conceivable that the sensor system 36 forms the presence detection unit 46.

Furthermore, an analog safety module, assembly unit B7, is integrated in the system 10. This includes, for example, two vacuum safety valves 48, each of which opening at an adjustable actual pressure value. It is also conceivable, however, that the safety module B7 has at least one electrical and/or electronic pressure limiting element and/or at least one pressure switch and/or at least one further pressure sensor.

Operating parameters, in particular desired values and/or target values and/or warning limits and/or maximum limits, can be displayed to the user via the display 20 which functions as an input and output means and may be designed as a touch screen, which operating parameters are also changed by the user and are displayed continuously or also on correspondingly selectable screens or displays which are interchangeable. FIG. 1 shows the display 20 in a state integrated in the housing 12 and flush with its outer surface.

The system 10 may further have an operating parameter recording module 50 which can be used to monitor and/or record operating parameters of the system 10. The operating parameter recording module 50 can be located on the system's 10 backend board 24 or control board 26.

The operating parameter recording module 50 may also have a patient data management interface 52 (cf. FIG. 3) which allows data to be exchanged with a patient data management system. For this purpose, the system 10 may comprise a corresponding interface, which here is formed by a common synchronization interface 54. It is also conceivable that the patient data management interface 52 communicates with other medical devices via wireless technologies. Here, the synchronization interface 54 is arranged in the cover plate left 28 and designed as a simple serial interface. It is also conceivable that the operating parameter recording module 50 may be realized by means of the synchronization interface 54. A stop signal or a stop command, for example, from other medical devices connected to the system 10 can be received via the synchronization interface 54. Furthermore, a stop signal or warning signal, for example, can be sent and/or passed on to other medical devices connected to the system 10. In addition, data can be exchanged via the synchronization interface 54.

This makes it possible, for example, to exchange a stop command for activating or deactivating the pressure regulation module B6 via the synchronization interface 54.

The system 10 may also have one or more sterile filters 56. The sterile filters 56 can be arranged in particular in the area of the supply line 40 and the discharge line 42 (cf. FIG. 4 and FIG. 6).

The system 10 also has a safe mode in which the supply line 40 is closed and at the same time the discharge line 42 is connected to the atmosphere.

In case of a system stop and/or in the event of a fault and/or loss of supply voltage, the safe mode is activated or can also be automatically activated. A corresponding functionality is stored in the control unit as well as in the electromechanical design.

A U-profile made of aluminum represents the main part of the housing 12. Provided on the rear side of the housing profile are four holes into which the multi-function holder 14 is screwed.

The multi-function holder 14 can therefore be mounted both horizontally and vertically. Examples of such attachments are in particular an attachment to a surgical stoplight (e.g. to a rail) or an attachment to a heart-lung machine (e.g. to a column).

The housing 12 also offers two mounting rails for an easy screwing of the mounting plates 58.

Furthermore, FIG. 2 shows that analog safety valves 48 are provided.

The analog vacuum safety valves 48 are designed to prevent the maximum desired negative pressure from being exceeded. These analog safety valves 48 may also be implemented by mechanical vacuum safety valves and be in fluid connection with the pressure regulating valve 38.

These mechanical vacuum safety valves 48 open at a specific, adjustable actual pressure value. The mechanical limitation ensures that a safe vacuum range is maintained, as the maximum negative pressure can be mechanically limited.

The vacuum safety valve can thus be configured in such a way that the maximum negative pressure cannot be exceeded.

For example, mechanical vacuum safety valves can be used to ensure that they open at maximum negative pressure. In particular, it is conceivable to integrate such valves with multiple redundancy in the system in order to be able to compensate for any undetected failure of system components, if possible.

For this reason, two analog safety valves 48 are provided in the embodiment shown in FIG. 2 in order to implement redundancy here.

Figure 3:
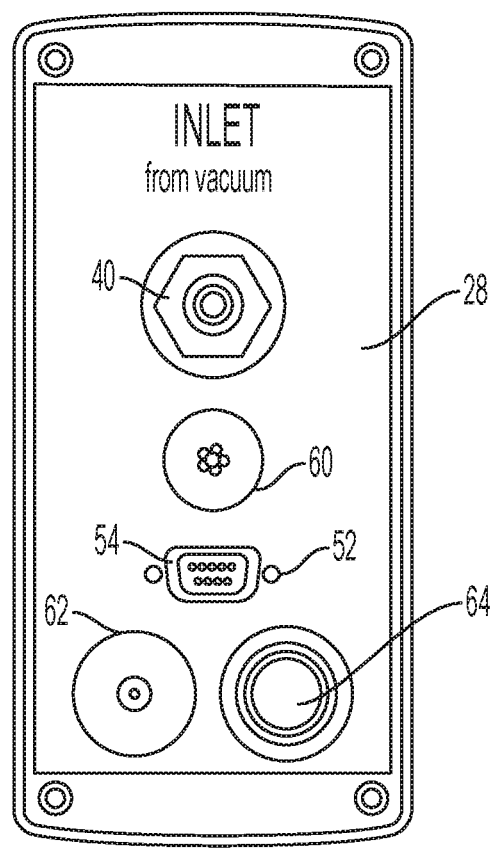
FIG. 3 is a more detailed representation of the primary interface (assembly unit B3) according to FIGS. 1 and 2.
Figure 4:
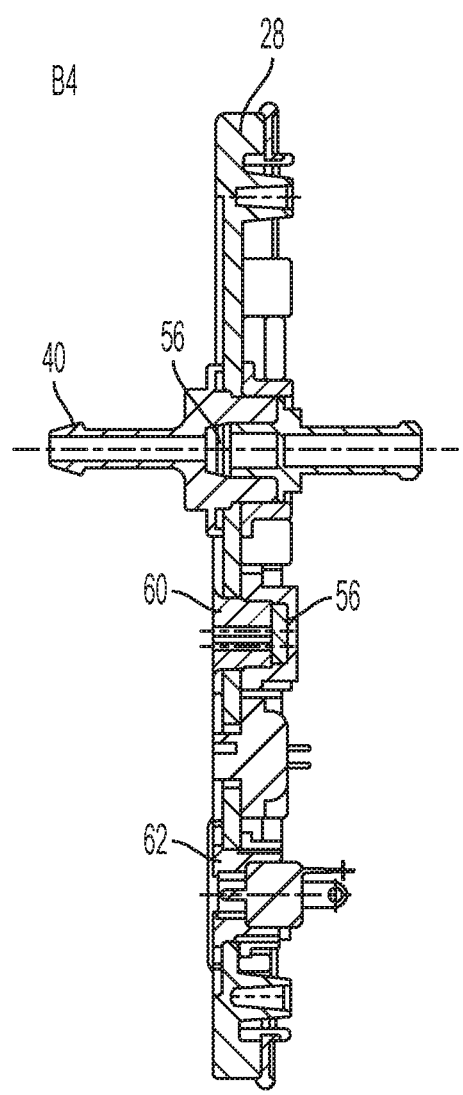
FIG. 4 is a sectional view of the primary interface according to FIGS. 1 and 2.

FIGS. 3 and 4 show the assembly unit B4 which has, among other things, the cover plate left 28, the supply line 40 (also provided with sterile filter 56 in this area) and a ventilation device 60 (also provided with a sterile filter 56 in this area). There is also a power connector 62 and a data interface which forms the synchronization interface 54.

The cover plate left 28 provides the interface to the environment, as shown in detail by the following components: among others, the power connector 62, the synchronization interface 54 and the vacuum supply line 40 are presented here.

In addition, according to FIGS. 2, 3 and 4, a switch-on/off button 64 for the system 10 with LED ring can be seen, arranged on the cover plate left 28.

This button 64 lights up green if the system 10 is in an activated and ready state and red when it is switched off but connected to a power source.

Basically, other colors or color combinations are also possible.

The lettering "INLET from vacuum" is engraved in the cover plate left 28.

The supply line 40 for the vacuum connection line is located directly below the lettering.

Figure 5:
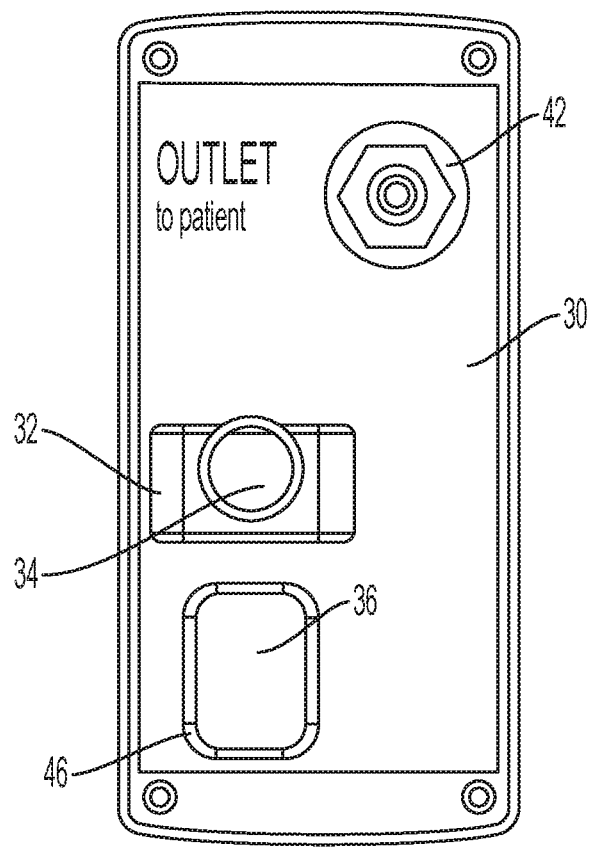
FIG. 5 is a detailed representation of the secondary interface (assembly unit B4) according to FIGS. 1 and 2.
Figure 6:
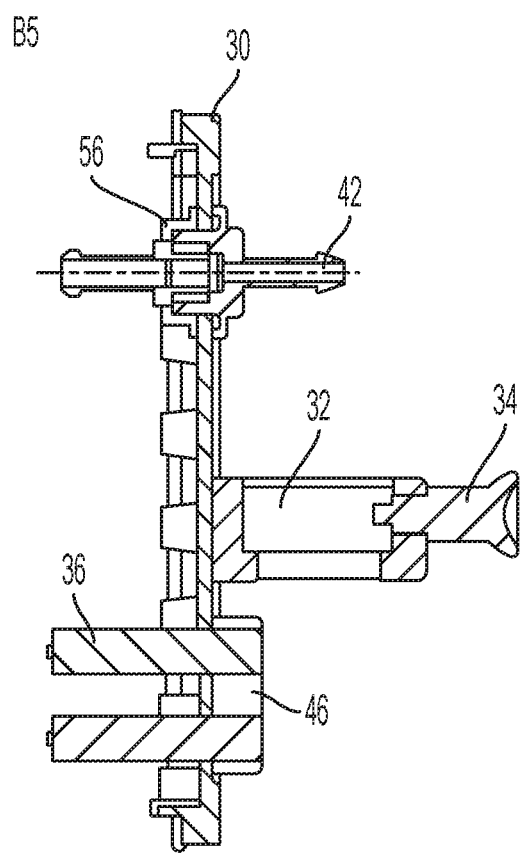
FIG. 6 is a sectional view of the secondary interface according to FIGS. 1 and 2.

FIG. 5 and FIG. 6 show the assembly unit B5, the secondary interface in a detailed and a sectional view. The vacuum discharge line 42 and the presence detection unit 46 can be seen here in detail. The lettering "OUTLET to patient" is engraved in the cover plate right 30.

Figure 7A:
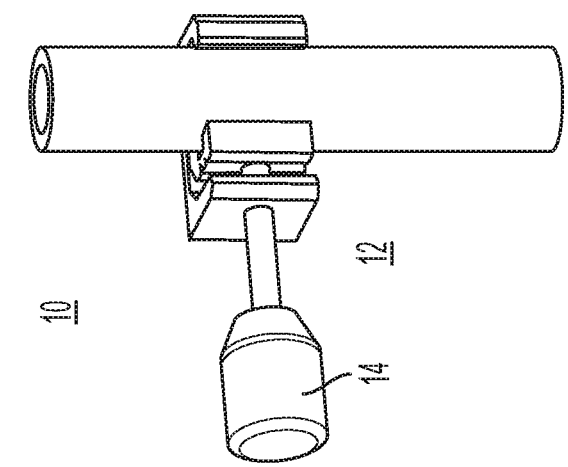
FIG. 7 shows a more detailed representation of horizontal and vertical mounting options via the retaining claw according to FIGS. 1 and 2.
Figure 7B:
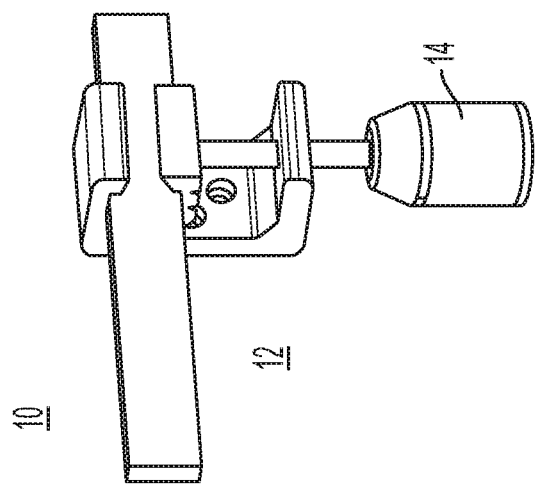

In addition, a detailed illustration of the horizontal and vertical mounting options of the multi-function holder 14 according to FIGS. 1 and 2 is shown in a perspective view in FIG. 7.

The multi-function holder 14 is attached horizontally to a square (e.g. an OP rail) as shown in the left diagram A in FIG. 7.

According to the right diagram B in FIG. 7, the multi-function holder 14 is fixed vertically to a tube (e.g. an HLM column).

The multi-function holder 14 can thus be mounted either in a vertically aligned or a horizontally aligned position on the housing 12 of the system 10, depending on the desired alignment.

Examples for such attachments of the multi-function holder 14 are in particular an attachment to a surgical stoplight or an attachment to a heart-lung machine (each not shown in FIG. 7).

In addition, the display 20 described above can be used to display various system-relevant information.

Figure 8:
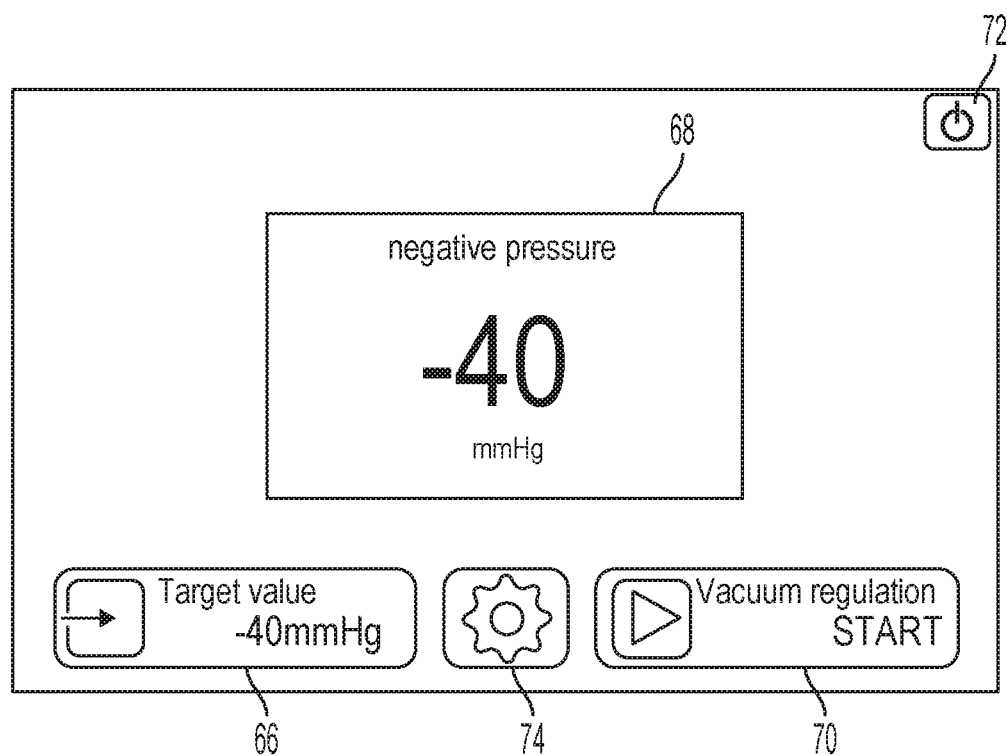
FIG. 8 shows a graphical representation of the main menu of the graphical user interface of the system shown by the display, including an overview of process parameters and system status as well as process settings which can be made.

FIG. 8 shows a graphical representation of the main menu of the graphical user interface. The adjustable target value 66 and the measured negative pressure 68 are clearly visible here. In addition, there are switch areas for starting the system (Start button 70), for switching off the system (Off button 72) as well as for navigating to the setup menu (Settings button 74).

FIG. 9 shows a graphical representation of the setup menu of the graphical user interface. Here, for example, settings can be made using the Maximum button 76, the Margin button 78 and the Language button 80. Submenus can be closed using the Close button 82.

FIG. 10 shows a graphical representation of a graphical user interface for entering a numerical value. This can be entered via the number keys 84. An input via sliders or arrow keys is also conceivable. By pressing the CE button 86, the entry can be deleted completely. The current entry is confirmed by pressing the OK button 88. The software is designed in such a way that it immediately checks all entries for plausibility. If the plausibility check fails, this is briefly signaled to the user and the next possible value is automatically set.

FIG. 11 shows a graphical representation of an error message on the graphical user interface. The error message is classified in the header line 90. The error is described in detail in the info area 92. A description can be made either purely via text, via graphics or via a combination of both. An output of error codes is also conceivable. An output of suggested solutions to the problem is also conceivable. Further information can be given in footer 94. The display of confirmation keys is also possible, for example if an error message requires a confirmation by the user.

The warning shown is displayed on the display 20 and serves to alert the user that there is fluid inside the fluid reservoir. To troubleshoot the problem, it is recommended to change the hose set.

Mounting the System

The individual assembly units are individually mounted and, after positive testing, assembled to form the overall product (i.e. system 10). For this purpose, the pressure regulation module B6 and the analog safety module B7 are screwed into the housing B1, and the vacuum lines of the primary interface B4 and secondary interface B5 are connected. The sensor lines are connected to the control unit B3 before the front cover B2 is clicked in place onto the housing B1. Finally, the primary interface B4 and secondary interface B5 are screwed to the housing B1, whereby it is tightly closed and sealed.

Preparation of the System

The system 10 is securely fastened in the operating room with the multi-function holder. Here, the columns of the HLM or at an OP stoplight are particularly suitable. Another mounting location is also conceivable. However, it must be ensured that the supply line 40 of system 10 can be connected to the house vacuum network or a vacuum pump or vacuum reservoir using a vacuum hose. The system 10 must also be connected to the voltage supply system via a Schuko socket. A corresponding power supply unit is connected to the power connector 62 and the Schuko socket. It must also be ensured that the system 10 is mounted in close proximity to the HLM to be able to ensure that the tubing set can be connected to both the discharge line 42 and the HLM reservoir.

Turning on the System and Test Routines

The system 10 is switched on at the main switch or the switch-on/off button 64. The system 10 first carries out an automatic self-test in which the following parameters are checked among others: The electronics and the internal connections, the operating hours since the last maintenance and the state of the system memory. If the self-test has been run without errors, the user performs a multi-stage check of the presence detection unit 46. The user is guided step by step through the test by instructions on the device.

Preparation of the Hose Set

The sterilely packed tubing set (not shown in the Figures) must be unpacked without contaminating the connections and the inside of the tubing.

Connecting the Tubing Set to the HLM

The protective cap (e.g. colored blue) of the tubing set is removed and connected to the cardiotomy reservoir of the heart-lung machine HLM. Connections are available on all products available on the market for this purpose.

Connecting the Tubing Set to the System

First, the reservoir of the tubing set is fixed in the intended holder of the system 10 as soon as the system requests to do so. For this purpose, the locking pin is retracted and the reservoir is inserted into the hole. The locking pin engages at a place above the lid of the reservoir and thereby fixes it in place. The protective cap (e.g. colored white) is then removed and the end of the hose is pushed over the vacuum discharge line 42 on the system 10.

Setting the Desired Negative Pressure

If necessary, the preset negative pressure can be set via the user interface.

In this case, FIG. 10 shows a graphical representation of the user interface, which is indicated by the display 20. Here, the target value can be entered numerically.

Furthermore, a maximum negative pressure value, a negative pressure tolerance range and a language can both be displayed and set in the form of fields, as shown in FIG. 9.

Start of the System

When all parameters have been set and the desired negative pressure has been adjusted and the hose set has been connected correctly, the system 10 can be started by pressing the Start button 70.

Stopping the System

If the system 10 is no longer needed, it can simply be stopped by tapping the start button. The system 10 is then immediately set to the safe state. To switch off the system 10 completely, it is necessary to press the Off button for a longer time (>3 seconds). The system 10 archives all log data and goes to the safe state. The user is then informed that it is now possible to safely switch off the system 10 via the switch-on/off button 64.

Removing the Hose Set

Finally, the hose set is removed and discarded.

REFERENCE NUMERALS 10 system
12 housing
14 multi-function holder
16 front cover
18 housing cover
20 display
22 touch controller
24 backend board
26 control board
28 cover plate left
30 cover plate right
32 reservoir holder
34 quick release mechanism
36 sensor system
38 pressure regulating valve
40 supply line
42 discharge line
44 pressure sensor
46 presence detection unit
48 vacuum safety valves
50 operating parameter recording module
52 patient data management interface
54 synchronization interface
56 sterile filter
58 mounting plate
60 ventilation device
62 power connector
64 switch-on/off button
66 target value
68 measured negative pressure
70 Start button
72 Off button
74 Settings button
76 Maximum button
78 Margin button
80 Language button
82 Close button
84 number keys
86 CE button
88 OK button
90 header line
92 info area
94 footer

The invention claimed is:

1. A system for vacuum-assisted venous drainage, comprising:
at least one pressure regulating module that includes at least one active pressure regulating valve comprising at least one controllable proportional pressure valve having at least one supply line and at least one discharge line, and at least one pressure sensor that is integral to the controllable proportional pressure valve, by means of which pressure in a region of the pressure regulating valve is monitored and an actual pressure value is detected, and the pressure regulating valve designed and set up in such a way that negative pressure generated by the pressure regulating module is actively regulated by means of the pressure regulating valve on the basis of the actual pressure value in the region of the pressure regulating valve as sensed by the pressure sensor integral to the controllable proportional pressure valve,
an input and output device by means of which operating parameters are input by a user and are output by means of the operating parameters,
an operating parameter recording module by means of which the operating parameters are monitored and/or recorded, and wherein the operating parameter recording module has a patient data management interface by means of which data is exchanged with a patient data management system,
a hose set for fluid guidance between the discharge line of the system and a reservoir to be regulated, and
a presence detection unit (PDU), wherein a correct placement and a correct connection of the hose set is monitored and/or verified by means of the PDU, wherein the hose set has at least one liquid reservoir and in that the correct placement and the correct connection of the liquid reservoir is monitored and/or verified by means of the PDU, and further wherein the PDU is configured to detect penetration of fluids into the at least one liquid reservoir and report said penetration to a control board.

2. The system according to claim 1, wherein the pressure regulating valve has at least one electrical and/or electronic pressure limiting element.

3. The system according to claim 1, wherein the system has sterile filters, inlets and outlets of the system and the supply line and the discharge line of the system being sterilely sealed by means of the sterile filters.

4. The system according to claim 1, further comprising at least one mechanical vacuum safety valve which is in fluid connection with the pressure regulating valve and opens at an adjustable actual pressure value.

5. The system according to claim 1, wherein the operating parameters are desired values and/or target values and/or warning limits and/or maximum limits; and wherein the operating parameters are displayed.

6. The system of claim 1, further comprising a controller configured to control the at least one pressure regulating valve, and wherein the pressure sensor is an electronic sensor comprising sensor lines connected to the controller.

7. The system according to claim 1, wherein the operating parameters are desired values and/or target values and/or warning limits and/or maximum limits; and wherein the operating parameters are displayed.

8. A system for vacuum-assisted venous drainage, comprising:
a housing,
at least one pressure regulating module arranged in the housing that includes at least one active pressure regulating valve comprising at least one controllable proportional pressure valve having at least one supply line and at least one discharge line, and at least one pressure sensor that is integral to the controllable proportional pressure valve, by means of which pressure in a region of the pressure regulating valve is monitored and an actual pressure value is detected, and the pressure regulating valve designed and set up in such a way that negative pressure generated by the pressure regulating module is actively regulated by means of the pressure regulating valve on the basis of the actual pressure value in the region of the pressure regulating valve as sensed by the pressure sensor integral to the controllable proportional pressure valve, a synchronization interface by means of which data is exchanged with one or more medical devices via the synchronization interface, the data including a command for activating or deactivating the pressure regulating module from the one or more medical devices, and a presence detection unit (PDU), wherein a correct placement and a correct connection of a hose set for fluid guidance between the at least one discharge line and a reservoir to be regulated is monitored and/or verified by means of the PDU, wherein the hose set has at least one liquid reservoir and in that the correct placement and the correct connection of the liquid reservoir is monitored and/or verified by means of the PDU, and further wherein the PDU is configured to detect penetration of fluids into the at least one liquid reservoir and report said penetration to a control board arranged in the housing.

9. The system according to claim 8, wherein the synchronization interface comprises a serial interface positioned on the housing, and wherein the system further comprises an integrated display on the housing configured to display a graphical user interface.

10. The system according to claim 8, wherein the pressure regulating valve has at least one electrical and/or electronic pressure limiting element, and wherein the one or more medical devices comprise a heart-lung machine.

11. The system according to claim 8, wherein the system has sterile filters, inlets and outlets of the system and the supply line and the discharge line of the system being sterilely sealed by means of the sterile filters.

12. The system according to claim 8, further comprising at least one mechanical vacuum safety valve which is in fluid connection with the pressure regulating valve and opens at an adjustable actual pressure value.

13. The system of claim 8, further comprising a controller configured to control the at least one pressure regulating valve, and wherein the pressure sensor is an electronic sensor comprising sensor lines connected to the controller.

14. A system for vacuum-assisted venous drainage, comprising:
a housing,
at least one pressure regulating module arranged in the housing that includes at least one active pressure regulating valve comprising at least one controllable proportional pressure valve having at least one supply line and at least one discharge line, and at least one pressure sensor that is integral to the controllable proportional pressure valve, by means of which pressure in a region of the pressure regulating valve is monitored and an actual pressure value is detected, and the pressure regulating valve designed and set up in such a way that negative pressure generated by the pressure regulating module is actively regulated by means of the pressure regulating valve on the basis of the actual pressure value in the region of the pressure regulating valve as sensed by the pressure sensor integral to the controllable proportional pressure valve, wherein the system has a safe mode in which the supply line is closed and at the same time the discharge line is connected to the atmosphere, and
a presence detection unit (PDU) mounted on the housing, wherein a correct placement and a correct connection of a hose set to the discharge line is monitored and/or verified by means of the PDU, wherein the hose set has at least one liquid reservoir and in that the correct placement and the correct connection of the liquid reservoir is monitored and/or verified by means of the PDU, and further wherein the PDU is configured to detect penetration of fluids into the at least one liquid reservoir and report said penetration to a control board arranged in the housing.

15. The system according to claim 14, wherein the safe mode is automatically activated in the event of a system stop and/or a fault and/or loss of supply voltage, and wherein the hose set is configured to fluidly couple the discharge line to a cardiotomy reservoir of a heart-lung machine and the liquid reservoir is configured to be accommodated by a holder mounted on the housing near the PDU.

* * * * *